United States Patent [19]
Verma

[11] Patent Number: 5,395,006
[45] Date of Patent: Mar. 7, 1995

[54] FERMENTATION VESSELS AND CLOSURES THEREFOR

[76] Inventor: Kuldeep Verma, 3509 Crofton Ct., Raleigh, N.C. 27604

[21] Appl. No.: 84,794

[22] Filed: Jun. 29, 1993

Related U.S. Application Data

[63] Continuation-in-part of Ser. No. 055,506, Apr. 29, 1993.

[51] Int. Cl.⁶ .......................... C12M 1/24; B65D 51/16
[52] U.S. Cl. ..................................... 220/371; 215/261; 215/306; 215/308; 215/310; 215/313; 220/231; 220/253; 220/367; 422/101; 422/102; 435/284; 435/296
[58] Field of Search ............... 435/284, 285, 296, 311, 435/313; 422/99, 101, 102; 215/307, 308, 336, 344, 261, 306, 310, 313; 220/231, 236, 253, 366, 373, 374, 371, 367

[56] References Cited

U.S. PATENT DOCUMENTS

| | | | |
|---|---|---|---|
| 4,224,765 | 9/1980 | Song | 47/85 |
| 4,271,973 | 6/1981 | Quagliaro et al. | 215/308 |
| 4,643,881 | 2/1987 | Alexander et al. | 422/265 |

Primary Examiner—David A. Redding
Attorney, Agent, or Firm—Olive & Olive, P.A.

[57] ABSTRACT

A closure device for fermentation test tubes or flasks (vessels) comprises a cylindrical cap which is either molded integrally with the vessel as one piece or is molded separately and is snugly fitted over the neck of the vessel, in a fashion which not only allows for free gaseous flow between the contents of the vessel and the ambient atmosphere but also facilitates easy access to the contents of the vessel without having to detach the closure from the vessel. Particular features of the cover permit manipulation with the fingers of the hand holding the vessel. Embodiments disclosed include those adapted to function selectively in aerobic or anaerobic procedures.

13 Claims, 10 Drawing Sheets

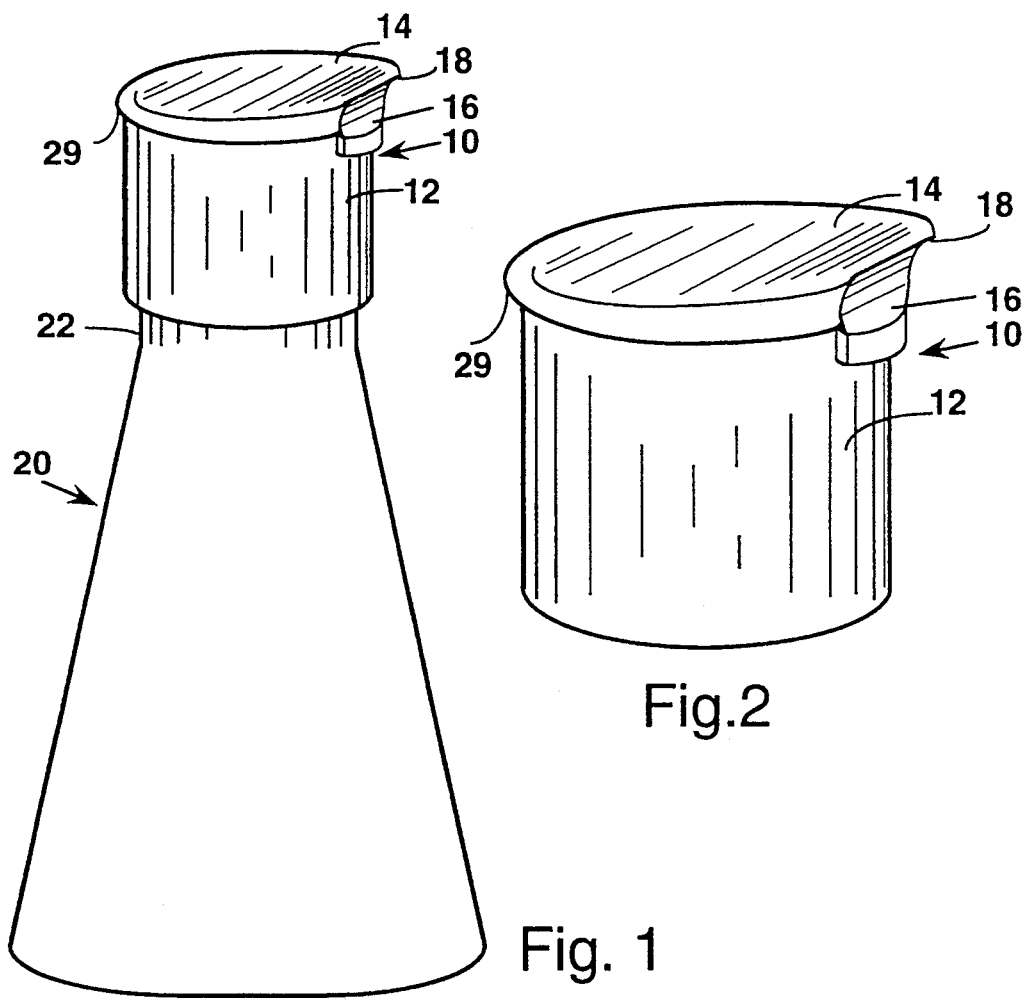
Fig. 1
Fig. 2
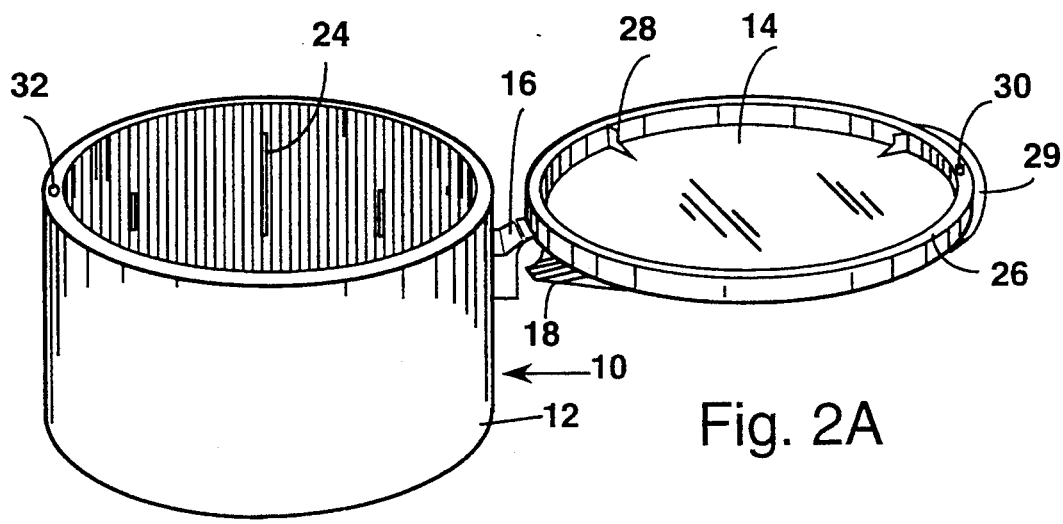
Fig. 2A

FERMENTATION VESSELS AND CLOSURES THEREFOR

This is a continuation-in-part of U.S. patent application Ser. No. 08/055,506, filed Apr. 29, 1993 and entitled FERMENTATION VESSELS AND CLOSURES THEREFOR.

BACKGROUND OF THE INVENTION

1. Field of the Invention

The present invention relates to fermentation vessels and closure devices for such vessels. More particularly, the present invention concerns fermentation vessels and specifically to fermentation vessels having closure devices which permit easy access to the vessel contents and also allow free exchange of gases between the contents and the ambient atmosphere.

2. Background of the Art

Fermentation processes, particularly cell or tissue culture procedures, are employed in a wide variety of research activities ranging from textiles to pharmaceuticals. Biotechnology research makes extensive use of fermentation procedures, which in general involve growth of a single purified strain of micro-organism with a goal of obtaining more cells or purifying the byproducts. The isolation of pure strains of microorganisms is a detailed process involving many steps. A newly identified colony of a particular microorganism is first transferred from a petri dish culture to a separate vessel containing appropriate nutrients. This microorganism is typically transferred several times to a new petri dish or a culture tube until the culture is free of contamination by other undesired strains of microorganisms. After purification of the strain, one needs to study the nature of this newly isolated strain of microorganism. For this purpose, one needs to grow it in a selected medium. The medium is inoculated with the microorganisms and placed in an incubator with a rotary shaker at a suitable temperature and for a period of time sufficient to permit growth of the microorganism culture. New nutrients or chemicals are added to the actively growing culture to impose selection pressure, or the new microorganism is sampled many times through the growth period for analysis and the consumed quantity of the nutrient medium is replenished. These operations require inoculation of a culture in the vessel by means of a sterile inoculation loop inserted through the mouth of the culture vessel so as to touch the medium inside. Similarly, sampling of the contents during the growth period requires introduction of sterile sampling devices into the active culture. Good laboratory practice dictates that all apparatus involved with a procedure viz. the closure, the vessels the inoculation loop and the samplers must be sterile to avoid contamination by exogenous microorganisms. All of these operations according to known practice, require manipulation of the vessel, the closure and a transfer loop or pipette with interchanging of functions involving both of the worker's hands. This process is cumbersome and needs lot of experience to accomplish without error, particularly when one has to handle multiple vessels. The vessel is typically in the form of a test tube or flask.

Ordinarily, laboratory experiments are conducted in groups having ten sample vessels. With the prior art type of vessel, the worker has to perform the following series of operations for each vessel:

1. lift the vessel from the rack with a first hand;
2. remove the cap with a second hand;
3. place the cap somewhere in the work area, which itself must be kept sterile;
4. place the vessel in the rack to free both hands;
5. open a petri dish containing a culture using both hands;
6. pick up the culture sample from the petri dish with a sterile loop with the second hand;
7. inoculate sample in the vessel;
8. set the inoculating loop down to free the second hand;
9. look for the same cad to avoid cross contamination; and
10. replace the cap on the vessel using two hands.

To perform the test procedure on a ten vessel typical batch, one must perform one hundred steps according to the prior art method. it is necessary to remove and replace the cap on the vessel with two hands because of the tight fit required.

The vast majority of microorganisms useful in commercial viable fermentation processes are aerobic microorganisms; that is, microorganisms which require oxygen to carry on their metabolic processes. In fact, the very purpose of shaking or stirring fermentation broths is to ensure effective mixing of air with the liquid culture medium. As a result, any closure device employed in the culturing of aerobic microorganisms must permit the passage of air into the vessel and the discharge of gaseous fermentation byproducts from the vessel while maintaining the sterility of the vessel contents.

In the past it has been the widespread practice to close the fermentation vessel with porous closures such as a sterile cotton plug or a synthetic material such as foamed polyethylene or styrene etc. More recently, stainless steel and plastic cap closures have become available which fit over the mouth of the fermentation vessel and permit the passage of gases into and out of the fermentation vessel. Examples of such closures are KIM-KAP closures and KAP-UTS plastic closures available from Owens-Illinois and BELLCO stainless steel closures available from Bellco Technology. These closures each have an internal diameter slightly larger than that of the neck of the fermentation vessel and fit snugly over the vessel mouth by means of fingers or ridges on the inside vertical walls of the closures. Small fins inside the closure prevent the top of the closure from seating against the top of the fermentation vessel, thus permitting the passage of gases into and out of the vessel while maintaining the sterility of the vessel contents.

A disadvantage of these prior art closures, whether of the porous plug type or the snug fitting cap closure type, is the need to completely detach the closure in order to gain access to the fermentation vessel contents. Each removal of the closure provides the potential for contamination of the vessel contents and requires flaming or other sterilization treatment of the vessel mouth and closure to ensure sterility which adds to the amount of work required of the laboratory technician per unit vessel. A further style of prior art closure for a fermentation vessel is disclosed in U.S. Pat. No. 5,116,758 to the present inventor for a FERMENTATION VESSEL CLOSURE. The prior '758 patent addresses certain of these problems, but leaves others unresolved.

Thus, there is a need in the fermentation are for efficient fermentation vessels and closure devices which not only permit easy and direct access to the fermentation vessel contents without the need to remove the closure device but also allow for gaseous exchange.

Therefore, it is the principal object of the invention to provide a one piece closure, all portions of the closure being integral with each other and which may be opened and closed with the hand holding the vessel typically in the form of a test tube or flask.

Another object of the invention is to provide a fermentation vessel which can be molded integrally with an easily opened and closed closure cap.

Another object is to provide a fermentation vessel having a closure which permits easy access to the vessel contents and allows gaseous exchange.

The foregoing and other objects will become apparent as the description proceeds.

SUMMARY OF THE INVENTION

The present invention provides a new type of closure device for fermentation vessels which permits access to the contents of the vessel without requiring complete removal of the closure and further permits the passage of gases into and out of the vessel while maintaining the sterility of the contents. In one embodiment, an outer cylinder member of greater diameter than the outer diameter of the neck or mouth of the vessel is molded, integral with the vessel as one piece, with intervening space maintained by ridges running along the inside length to allow for gases to flow. The outer cylinder member bears a movable closure at the capping end. Alternately, the closure device of this invention may comprise a separate closure having a cylindrical wall portion open at one end and having at the other end thereof a cover. Means for engaging the mouth of a fermentation tube or flask are disposed along the inner surface of the cylindrical wall portion and stand off means for permitting the free flow of gases into and out of the capped fermentation vessel are disposed radially around the inner surface of the capping end. In this embodiment, the closure device is molded separately from the vessel.

In particular embodiments of the present invention disclosed herein, the closure is adapted for use in aerobic, i.e. with oxygen present, or in anaerobic, i.e. without oxygen present, procedures. One such embodiment provides one position for a closure to allow gas interchange and a second position to seal to the vessel neck. Another embodiment involves a rotatable disc with openable vents to allow gas interchange through a gas pervious material to the vessel interior, without requiring stand-off means.

The novelty and improvement in the fermentation vessel and closures of the present invention permit both gaseous exchange between the vessel contents and the outer atmosphere as well as free access to the fermentation vessel contents without requiring removal of the closure device. Furthermore, the closure is permanently molded and or snugly fitted to the container, so that one has only to deal with a pivotable or slidable cover at the capping end.

For purposes of comparison, with the new fermentation vessel closures described herein, one has to only perform these steps:

1. open the closure of the vessel with a first hand without removing the vessel from the rack;
2. open a petri dish containing a culture using both hands;
3. pick up a culture sample from the petri dish with a sterile loop with a second hand;
4. inoculate sample in the vessel;
5. set the inoculating loop down; and
6. close the closure of the vessel using two hands, without removing from the rack.

With the ten vessel typical test batch, one has to perform only sixty steps, saving forty steps in comparison to the prior known methods. Also, in the method of the invention, each hand has a specific function and the risk of cross contamination is sharply reduced.

BRIEF DESCRIPTION OF THE DRAWINGS

FIG. 1 is a perspective view of a fermentation vessel with a closure in accordance with a first embodiment of the present invention.

FIG. 2 is a perspective view of the fermentation vessel closure of FIG. 1 in the closed condition with the vessel not being shown for purposes of illustration.

FIG. 2A is a perspective view of the fermentation vessel closure of FIG. 1 in the open condition with the vessel not being shown for purposes of illustration.

DETAILED DESCRIPTION OF THE INVENTION

Figure 3:
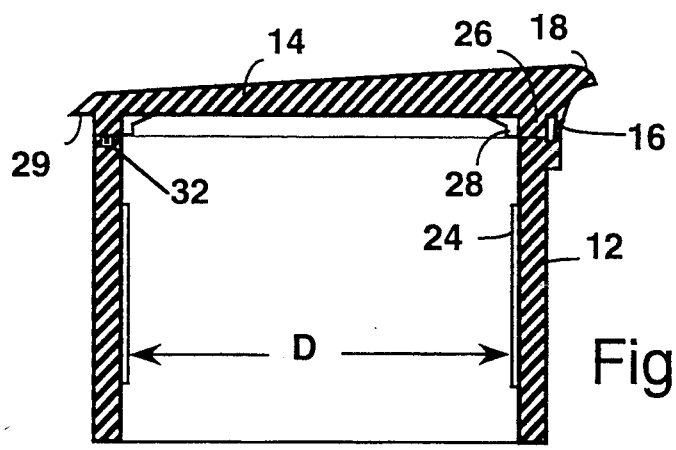
FIG. 3 is a cross sectional elevation view of the closure of FIG. 1 in the closed condition but with the vessel not being shown for purposes of illustration.

The fermentation test tube or flask incorporating the closure device of the invention permits covering of such a fermentation vessel so as to maintain the pre-established sterility of the contents while permitting access to the interior thereof to add to or remove from the vessel contents. The closure device establishes access through a one-hand manageable cover which permits transfer loops, pipettes and the like to be inserted into the fermentation vessel without removing the entire closure device. The closure device of this invention may be molded separately or integral with the fermentation vessel by conventional techniques well known in the molding arts of any suitable flexible resin which is capable of withstanding the temperatures required for autoclave sterilization. Suitable materials include synthetic polymers such as polyethylene, polypropylene, poly (tetraflouroethylene), polycarbonate, synthetic rubber and the like. A number of embodiments are illustrated and described below.

The closure of the present invention provides the convenience to the user of being able to hold the neck of a fermentation vessel and quickly and easily open (and close) the closure device using the finger or thumb of the hand holding the fermentation vessel and to carry out sampling or addition operations with the other hand. This one-hand capability simplifies the cumbersome procedure, associated with the prior art practice, of having one hand just for completely removing the closure to access the vessel contents and also to carefully place the detached closure in some sterile place to avoid contamination and, moreover, with a caution that the same closure has to be returned to the vessel to avoid cross contamination. Thus, while one hand just holds the fermentation vessel, the other hand has to do many operations. i.e., opening the closure, placing it in a sterile place, picking up the transfer loop or pipette for the required operation to be performed, releasing the loop or pipette to set this hand free for picking up the closure and closing the vessel. Thus, the existing closures are prone to risks of contaminations and errors and demand a lot of attention of the technician.

According to the previously discussed objectives and advantages of the present invention, a first embodiment thereof is illustrated in FIGS. 1, 2, 2A, 3, 4 and 4A. The primary unique advantage common to all embodiments of the invention is the ability of a user to open and close a closure cover with a single hand, thus leaving the second hand to perform other functions and while permitting the desired gas exchange. In FIG. 1, the separately molded closure 10 of the invention is shown mounted on a typical vessel, flask 20 having a neck 22. Collar 12 of closure 10 is attached to and closed by cover 14 by means of integral hinge 16 which is openable by a lever 18. An alternate opening structure is provided by lifter tab 29.

Figure 4:
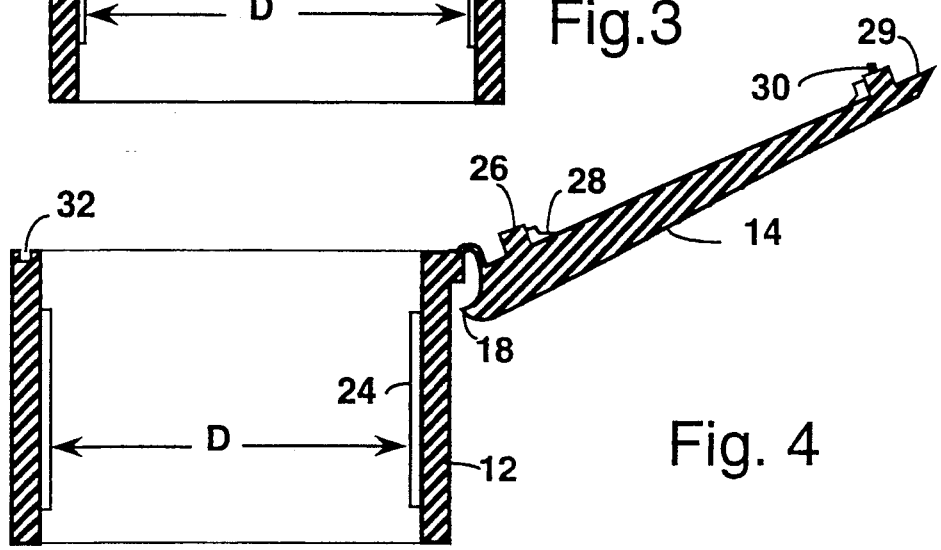
FIG. 4 is a cross sectional elevation view of the closure of FIG. 1 in the open condition but with the vessel not being shown for purposes of illustration.
Figure 4A:
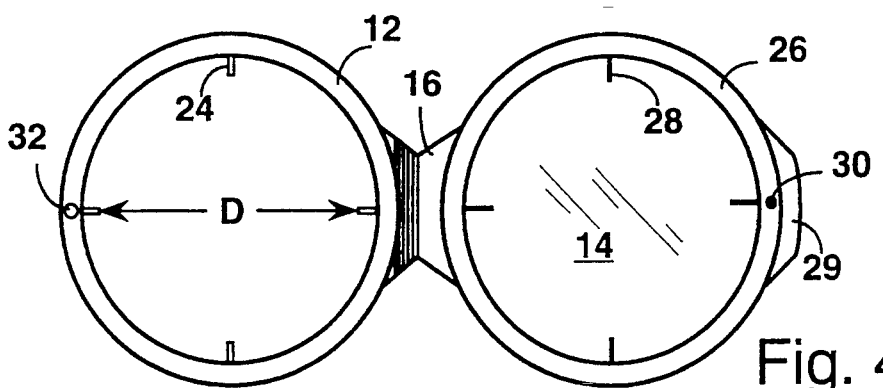
FIG. 4A is a top plan view of the closure of FIG. 1 but with the vessel not being shown for purposes of illustration.

Closure 10 is shown alone in FIG. 2 in perspective view, in FIG. 3 in cross sectional elevation as a closed unit, and in FIG. 4 as an open unit. In reference to the cross sectional views of FIGS. 3 and 4, and to views 2A and 4A, internally radiating standoffs 24 are dispersed about the inner circumference of collar 12 and terminate at a diameter D adapted to snugly fit over neck 22 of vessel 20 and maintain collar 10 in a selected position. Standoffs 24 serve to establish a series of gas exchange channels between neck 22 and collar 12 which is a relatively long and indirect path to minimize the chance of contamination. Cover 14 has a cover lip 26 of an essentially equal diameter to that of collar 12 and further has spacers 28 in a plurality of locations around the inner surface of cover 14 and adapted to keep cover 14 from sealing against the top of vessel 20 to permit the passage of air or other gases. Vessel 20 may be either a flask, test tube or other related laboratory container which is typically used in the intended process of culture fermentation.

It is preferred that the molding of closure 10 be accomplished in a manner so as to result in cover 14 being biased to remain open. Thus, when a laboratory technician presses down on the top of lever 18 or lifts tab 29 of closed cover 14, cover 14 springs to the open position. When the technician presses the top of cover 14 to a closed position, a lock pin 30 releasably engages a recess 32 to maintain cover 14 in the closed position, with spacers 28 keeping cover 14 from sealing against gas interchange.

Figure 5:
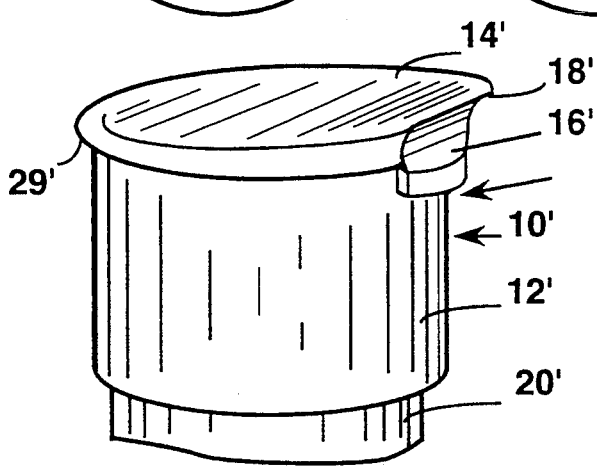
FIG. 5 is a perspective view of the fermentation vessel closure integrally molded with a partially illustrated fermentation vessel according to a second embodiment of the invention.
Figure 5A:
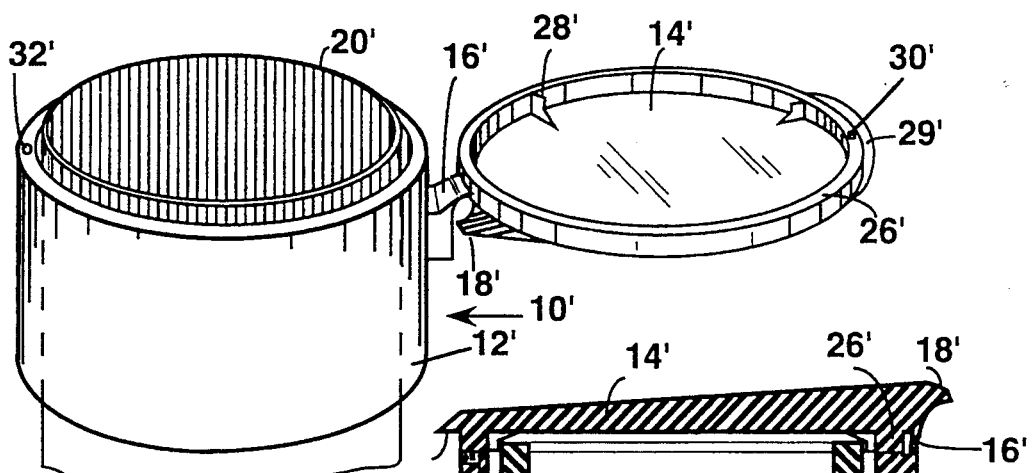
FIG. 5A is a perspective view of the closure and integrally molded vessel of FIG. 5 in the open condition.
Figure 6:
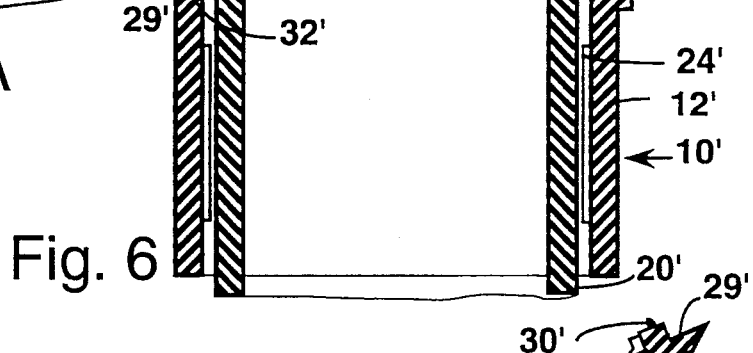
FIG. 6 is a cross sectional elevation view of the closure and vessel of FIG. 5 in the closed condition.
Figure 7:
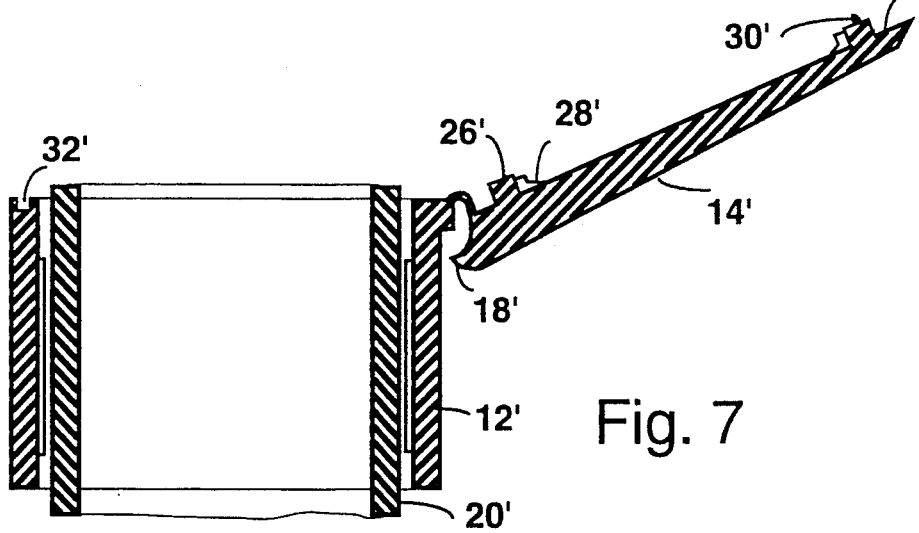
FIG. 7 is a cross sectional elevation view of the closure and vessel of FIG. 5 in the open condition.
Figure 7A:
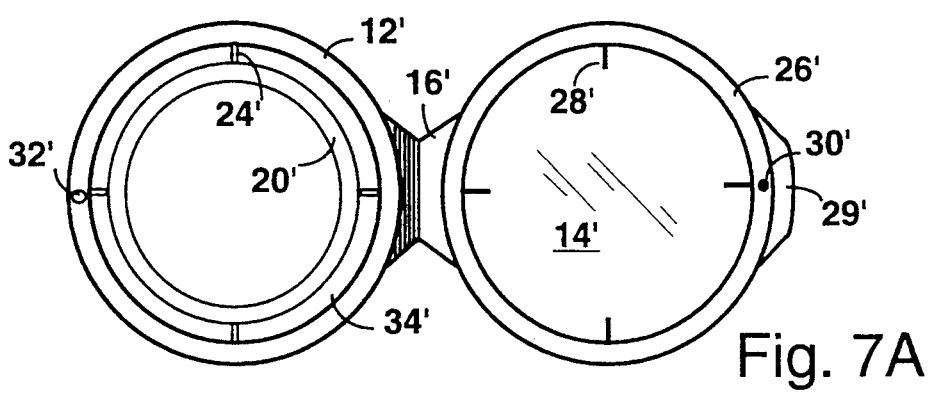
FIG. 7A is a top plan view of the closure and vessel of FIG. 5 in the open condition.
Figure 8:
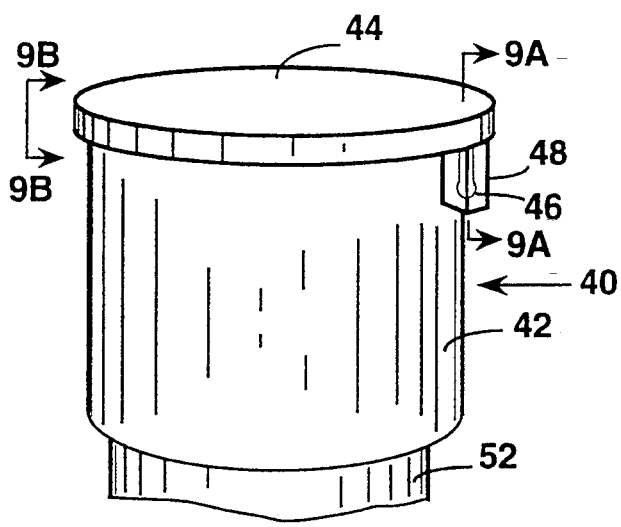
FIG. 8 is a perspective view of a fermentation vessel closure integrally molded with a partially illustrated fermentation vessel according to a third embodiment of the invention.
Figure 9A:
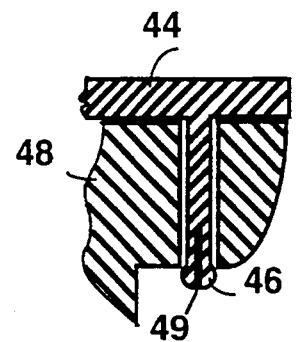
FIG. 9A is a partial cross sectional view taken in the direction of line 9A—9A of FIG. 8.
Figure 9B:
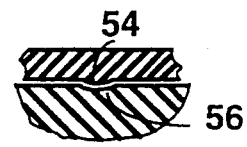
FIG. 9B is a partial cross sectional view taken in the direction of line 9B—9B of FIG. 8.
Figure 10:
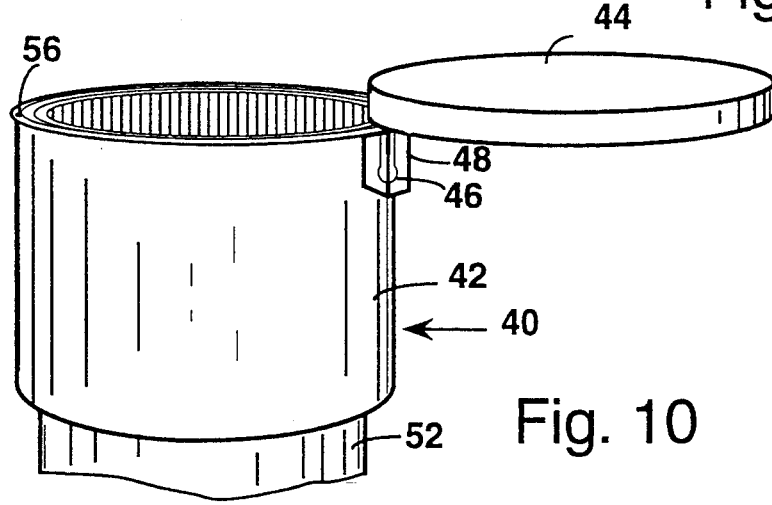
FIG. 10 is a perspective view of the closure and vessel of FIG. 8 in the open condition.

A different, but related second embodiment of the present invention is depicted in FIGS. 5, 5A, 6, 7 and 7A. The structure of the closure 10' of the second embodiment is similar to that discussed above, with the addition that closure 10' is molded integrally with the neck of vessel 20'. Thus, the closure and vessel become an integrally molded unitary structure. As shown in FIGS. 5A and 7, vessel 20' protrudes slightly above the top of collar 12' to allow more reliable and cleaner insertion of specimens and tools to the interior of vessel 20'. An air/gas channel 34 (FIG. 7A) is maintained between the respective walls of vessel 20' and collar 12' as is needed in carrying out an aerobic fermentation process.

FIGS. 8–14 are directed to two additional embodiments which operate differently than the first and second embodiments. According to the third embodiment, shown in respective closed and open views in FIGS. 8–10, collar 42 is integrally molded with vessel 52. Cover 44 is rotatably attached to the upper end of collar 42. Cover 44 is moved from the closed position (FIG. 8) to the open position (FIG. 10) by movement of a finger of the hand holding vessel 52 by pivoting around hinge pin 46. Detail of the assembly of hinge pin 46 integrally molded with cover 44 to collar 42 by means of boss 48 is shown in FIG. 9A. Pin 46 is molded with a snap-fit slotted end 49 as shown for simple assembly. Cover 44 is kept from accidental opening by the engagement of teeth 54 and depressions 56 as seen in FIG. 9B. In this embodiment, the upper end of collar 42 is equal to or higher than the height of vessel 52, and similar standoffs and air/gas channels are formed as those described above.

Figure 11:
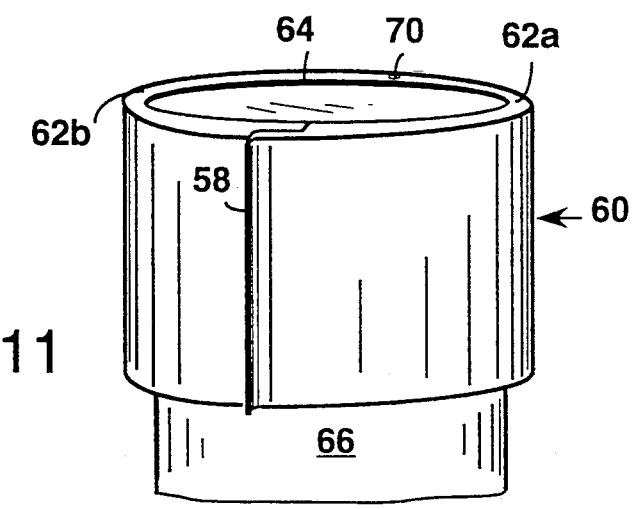
FIG. 11 is a perspective view of a fermentation vessel closure integrally molded with a partially illustrated fermentation vessel according to a fourth embodiment of the invention.
Figures 12, 15:
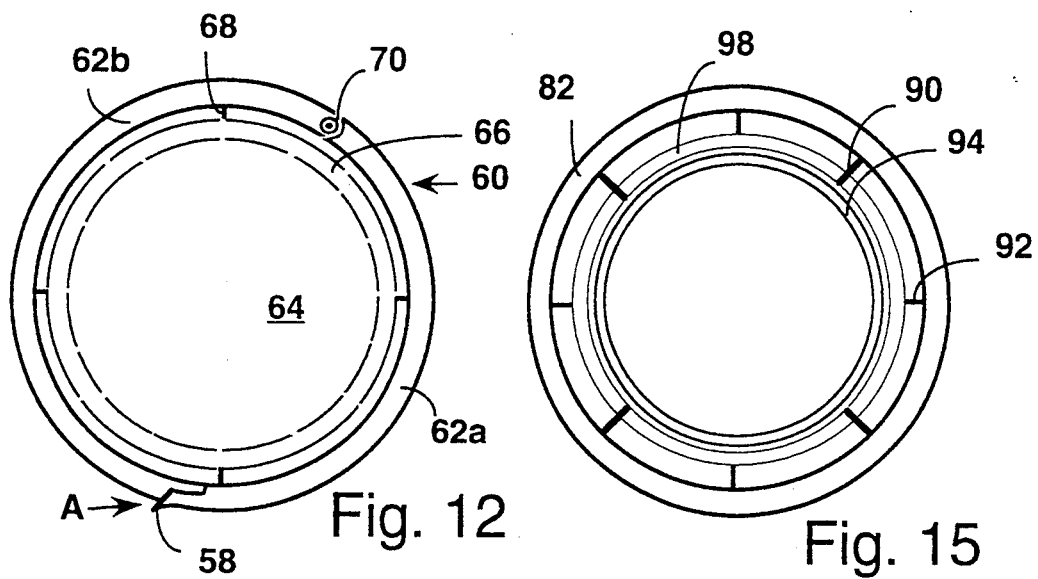
FIG. 12 is a top plan view of the closure and vessel of FIG. 11 in the closed condition.
FIG. 15 is a bottom plan view of the closure of FIG. 14.
Figure 13:
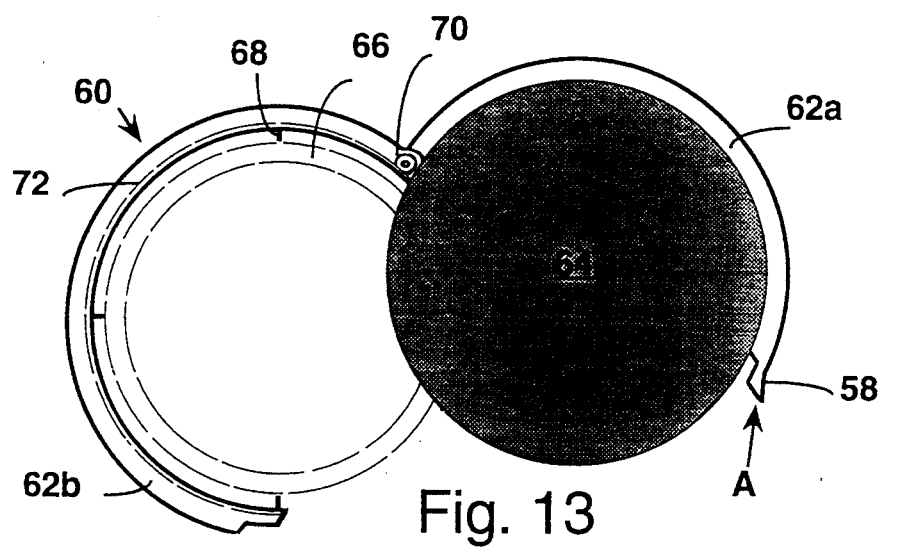
FIG. 13 is a top plan view of the closure and vessel of FIG. 11 in the open condition.

The fourth embodiment for exclusive use in aerobic fermentation is shown in FIGS. 11–13. In this case, collar 62 is divided into portions 62a and 62b. Fixed collar portion 62b is molded integral with, or subsequently adhered to, vessel 66; pivotal collar portion 62a is molded integrally at its upper end with cover 64 and assembled to fixed collar portion 62b by hinge pin 70. Collar portion 62b is formed with an undercut groove 72 adapted to receive the mating edge of cover 64 so as to minimize air infiltration and contamination. Tab 58 protrudes from the cylindrical contour of collar 62a, 62b as an aid in opening, as illustrated at arrow A in FIGS. 12 and 13.

Figure 14:
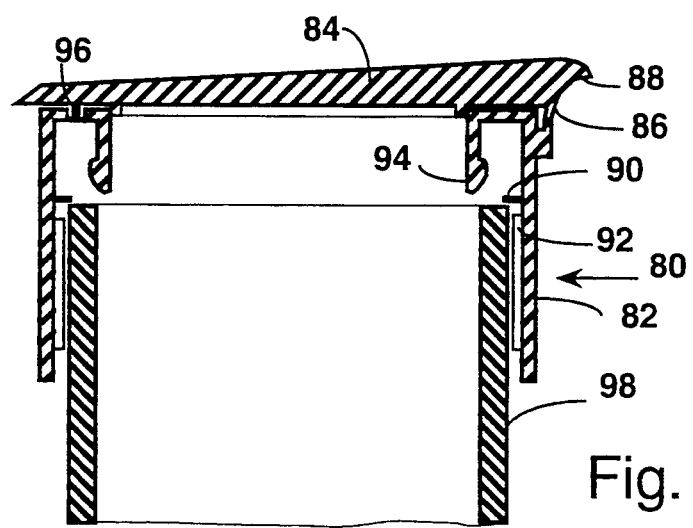
FIG. 14 is a cross sectional elevation view of a fermentation vessel closure according to a fifth embodiment of the invention and mounted onto a vessel neck.
Figure 16:
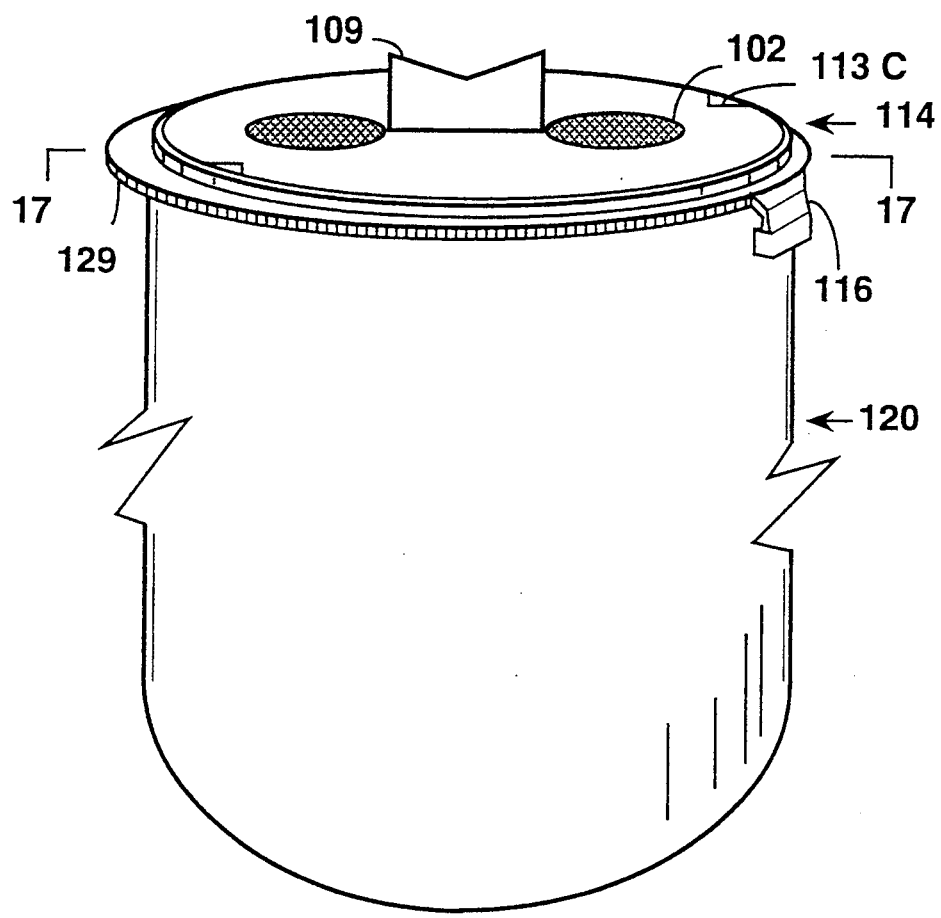
FIG. 16 is a perspective view of an aerobic—anaerobic fermentation vessel in accordance with a sixth embodiment of the invention including a closure cover incorporating a filter material, shown in closed position as arranged for aerobic fermentation.

Whereas the embodiments described above relate to uses in aerobic fermentation, there is also a need for a closure for a fermentation vessel in an anaerobic process which closure is manipulable with a single hand. The fifth embodiment illustrated in FIGS. 14 and 15 is adapted to function with either aerobic or anaerobic culture techniques. Closure 80 is formed as a separate unit from test tube, flask or other vessel 98 so as to be able to mount in two significant positions relative to the condition of air/gas passage. Stand off 92 is formed as previously described in a plurality of positions radially around the inside surface of collar 82. At approximately the upper end of the stand off 92, a series of flexible stops 90 are formed which protrude radially inwardly so as to contact the upper edge of vessel 98. When closure 80 is pressed onto the neck of vessel 98, stops control the depth of engagement without blocking air/gas flow. In this mode, closure 80 allows air/gas flow and operates aerobically as the earlier embodiments. If anaerobic processing is needed, further downward pressure on closure 80 will cause flexible stops 90 to yield and allow seal ring 94 to engage the inner surface of vessel neck 98 and prevent air/gas passage. Opening and closing is accomplished by manipulation of lever 88 about integrally formed hinge 86. A lock 96 to ensure the maintenance of a sealed condition of cover 84 is formed as disclosed in relation to the first and second embodiments of the invention.

A sixth embodiment, also providing aerobic as well as anaerobic capability, is illustrated in FIGS. 16 through 23 and comprises a closure 114 which is integrally molded at the open end of a vessel member neck portion 120. Closure 114 comprises the following parts, illustrated from top to bottom, in order (see FIG. 19):

(a) a substantially planar regulator disc A having a wall portion in which are formed a plurality of radially dispersed vents 102A symmetrically positioned about the central axis AX of the fermentation vessel neck 120, diametrically opposed notches 113A and upwardly facing knob 109;

(b) a filter disc B made of a gas pervious material and having diametrically opposed notches 113B which can be aligned with notches 113A mentioned above;

(c) a rotatable support wall C with vents 102C positioned similarly to vents 102A in the regulator disc A above, and having locking tabs 113C which are received in the mentioned notches and act to align the filter disc B and the vents 120A of regulator disc A with vents 102C of support wall C within the lip or rib 111. Regulator disc A, filter disc B and support wall C thus form an assembly which can be rotated on a cover base D to align or misalign the air vents 102A and 102C with respect to vents 102D of cover base D as per the desired aerobic or anaerobic gas interchange conditions of the experiment to be performed; and (d) a cover base D, also having complimentary vents 102D sized and positioned as in regulator disc A and body C above, a cup-like or rib formation facing upwards to house the rotatable assembly comprising the three components above it in nesting relation within cavity 107 with retaining rim 108 (see FIG. 17) and allowing their rotation as a unit up to a specified angle and, a lower rim or rib projecting downwardly configured to provide a snug, air-tight fit on the mouth of the culture vessel neck 120. The cover base D is integrally molded to vessel neck 120 adjacent to the mouth of vessel neck 120 by means of a connecting hinge 116, and cover base D also has a lifter tab 129 juxtaposed to hinge 116.

Figure 17:
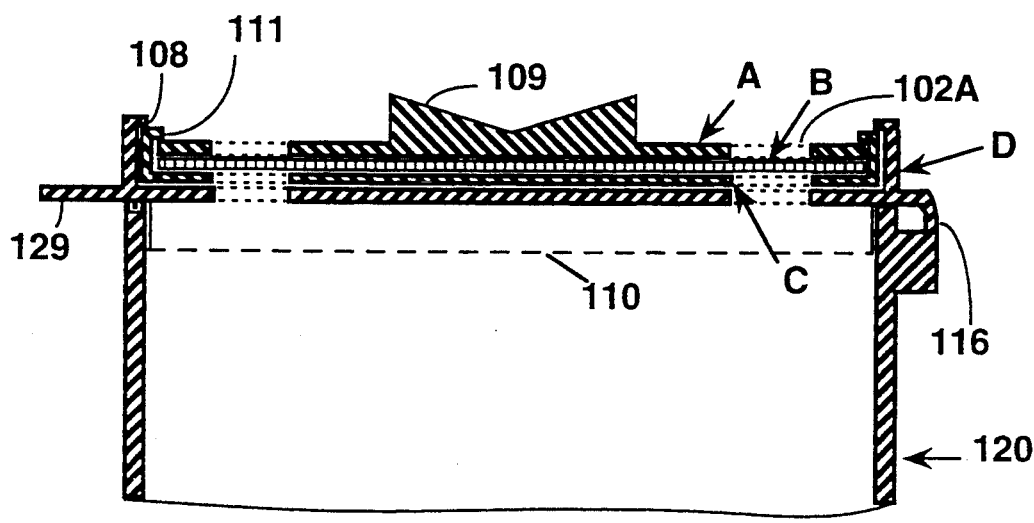
FIG. 17 is a cross sectional elevation view of the upper portion of the fermentation vessel of FIG. 16 taken generally in the direction of line 17—17 of FIG. 16.
Figure 18:
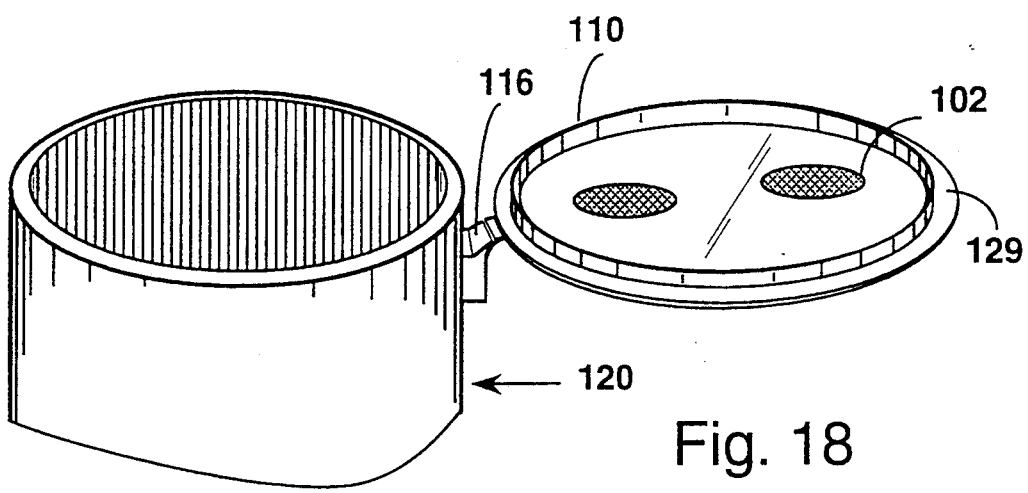
FIG. 18 is a perspective view of the upper portion of the fermentation vessel of FIG. 16 with the closure cover shown in the open position.
Figure 18A:
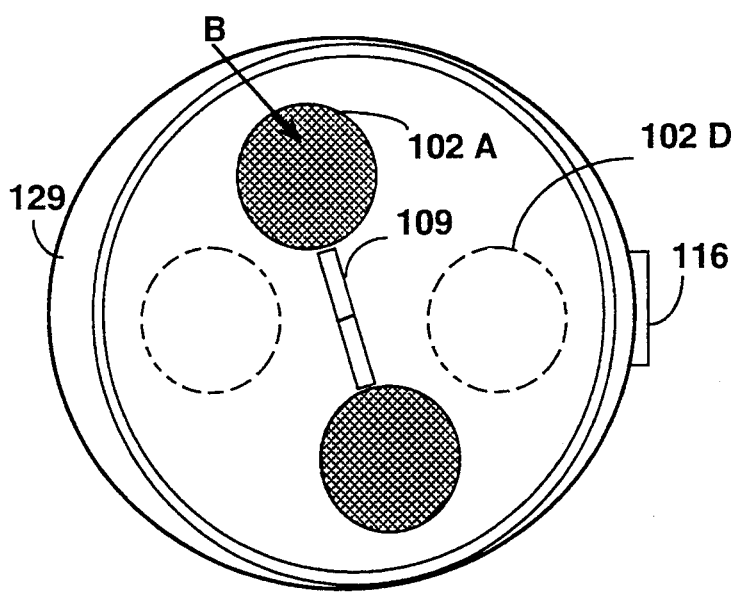
FIG. 18A is a top plan view of the fermentation vessel of FIG. 16 with its vents positioned for anaerobic use.
Figure 18B:
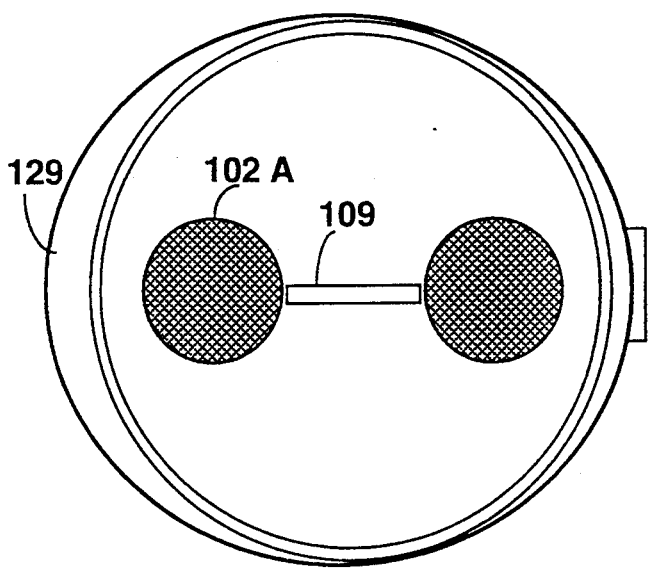
FIG. 18B is a top plan view of the closure of FIG. 16 with the vents positioned for aerobic use.
Figure 19:
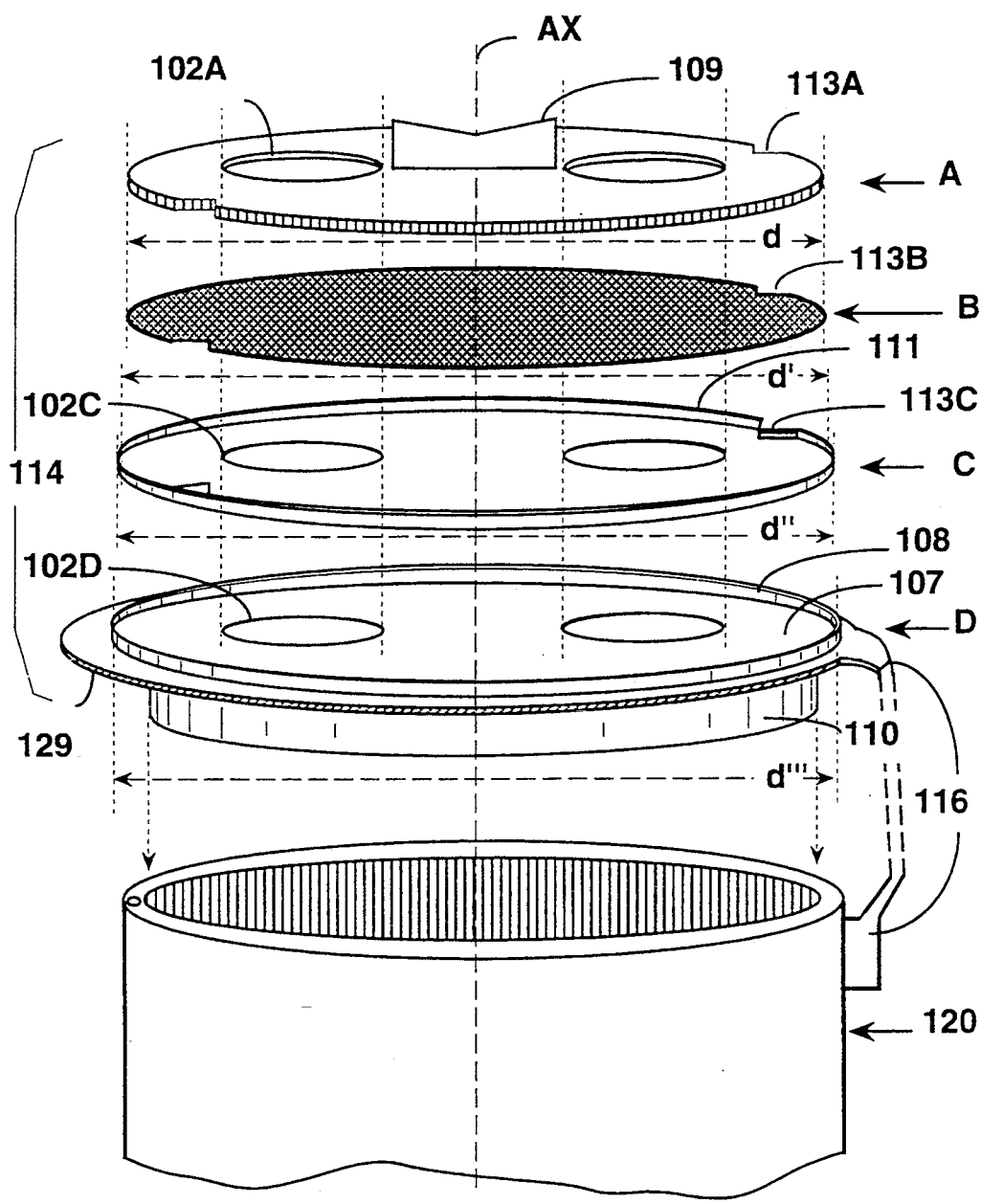
FIG. 19 is an exploded perspective view of the upper portion of the fermentation vessel of FIG. 16.
Figure 19A:
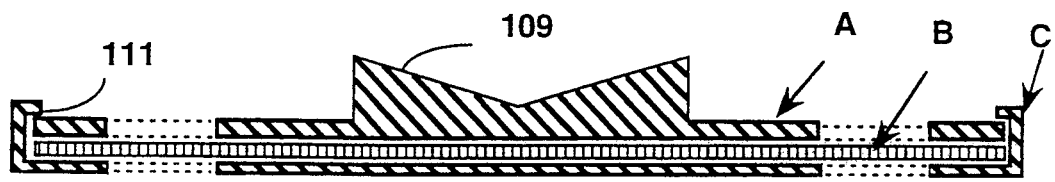
FIG. 19A is a cross sectional elevation view of the rotatable vent-filtration assembly.

Thus the gas pervious material of filter disc B is sandwiched between the regulator disc A and the circular body C to form a three-layer unit residing or nesting rotatably within lip 111. The plastic resin selected for regulator disc A and support disc C is sufficiently flexible to allow regulator disc A to snap into and be captured by lip 111, with the diameter d of regulator disc A being slightly greater than the inner diameter d' of support disc C lip 111. The three-layer unit A-B-C is placed on cover base D, is captured within cavity 107 by retaining rim 108 and rotates on cover base D as an assembly. The diameter d" of support disc C is slightly greater than the inner diameter d''' of cover base D lip 108 (FIG. 17). The rotation of the assembly comprising parts A, B and C is accomplished by turning upwardly facing knob 109 which is molded integrally with the regulator disc A. When the vents 102A and 102C in the rotatable assembly A-B-C are aligned with the vents 102D of the cover base D, the fermentation vessel is capable of acting as an aerobic chamber as shown in FIG. 18B and the gaseous exchange is able to take place through the intervening gas pervious material of filter disc B while still maintaining sterility within the fermentation vessel. Furthermore, when the alignment of vents 102A, 102C and 102D is interrupted by rotating the knob 109 to some selected angle, the fermentation vessel operates in the anaerobic mode as illustrated in FIG. 18A. The nature of gas pervious material is well known in the trade as a membranous or a porous shem and is left to the discretion of the designer. A pair of stops (not shown) are contemplated being molded into support disc C and cover base D to restrict their relative rotation to a selected angle.

Access to the interior of fermentation vessel 120 for extracting or inserting material is provided by pressing lifter tab 129 upwards and tilting the closure cover 114. The closure cover 114 is subsequently securely closed by mating of the air tight lower rim 110 of the body D with the mouth of the vessel neck 120 as shown in FIG. 17. Lower rim 110 may be configured to engage within (as illustrated) or without the fermentation vessel neck 120.

It is preferred that the molding of hinge 116 be accomplished so that closure cover 114 is biased to remain open. Thus, when one lifts tab 129, the cover springs to the open position and stays clear of the mouth of the vessel to provide easy access to the contents therein. When the user presses the top of closure cover 114 to a closed position, the lower rim 110 releasably engages the walls of the vessel neck 120.

Figure 20:
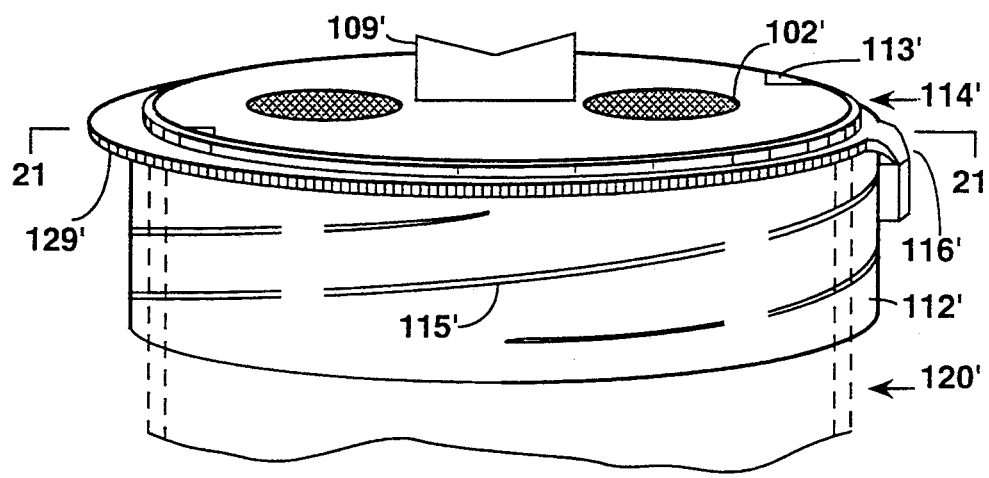
FIG. 20 is a perspective view of a fermentation vessel closure device adapted for aerobic—anaerobic use and shown mounted on the neck of a fermentation vessel (in dashed lines).
Figure 21:
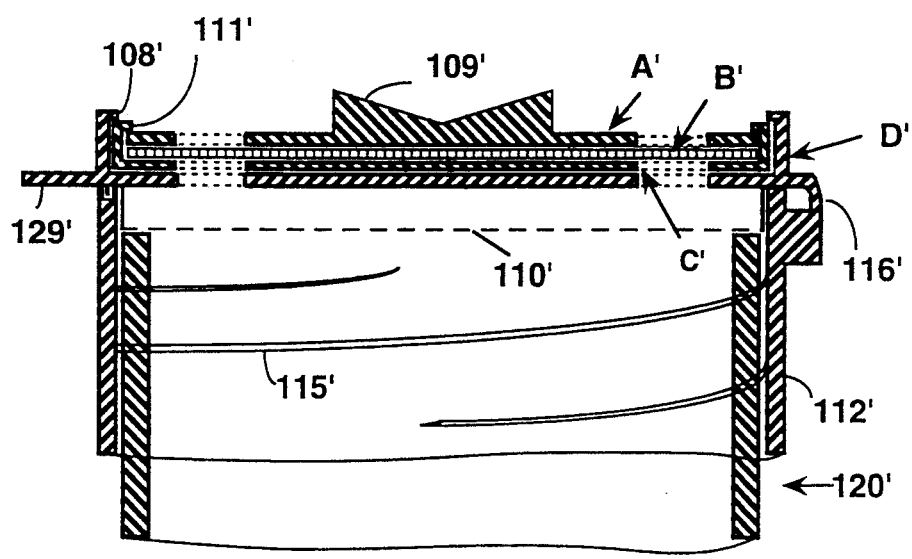
FIG. 21 is a cross sectional elevation view of the fermentation vessel closure device of FIG. 20 (in dashed lines) taken generally in the direction of line 21—21 of FIG. 20.

As described in relation to earlier embodiments of the invention, it is preferred in certain situations to adapt a separately formed closure to an open-top vessel for fermentation operations. FIGS. 20 and 21 illustrate cap 112' which is adapted to snugly fit the neck of separately formed fermentation vessel 120' by means of engagement of complementary male and female screw threads 115'. Cover portion 114', comprising regulator disc A', filter disc B', body C' and cover base D', similar to components illustrated in FIG. 19 and described above, is integrally connected to cap 112' by hinge 116'. Once assembled and mounted to vessel neck 120', the closure of this embodiment functions similarly to the integrally formed closure disclosed above per FIGS. 16–19.

To adapt these designs of closures to existing vessels which often have screw teeth on the neck, the closure has been provided with internal screw teeth 115' to loosely or tightly match with those on the vessel neck 120' as shown in FIGS. 20 and FIG. 21. With a somewhat elastic material forming cap 112', the screw threads 115' also seal snugly to a smooth neck 120' which does not have complimentary screw threads.

Figure 22:
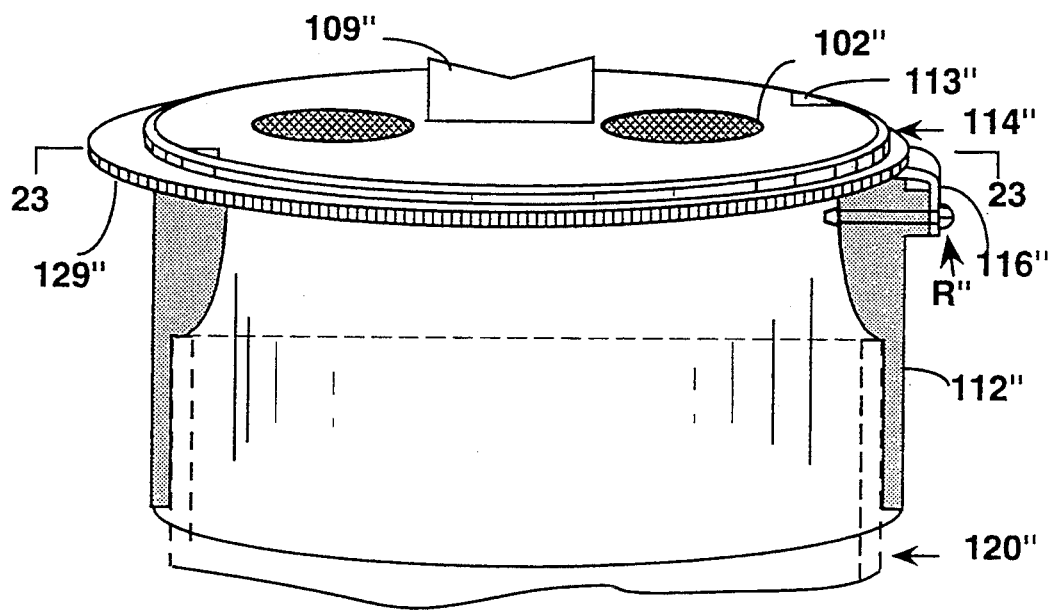
FIG. 22 is a perspective view of a fermentation vessel closure substantially as in FIG. 20 except that the body of the closure is made of flexible elastic material.
Figure 23:
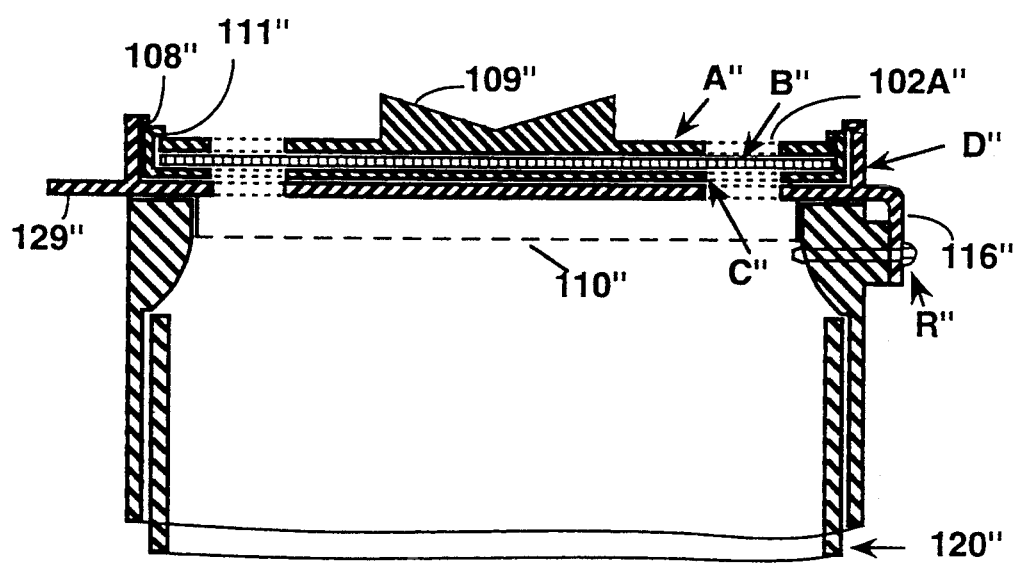
FIG. 23 is a cross sectional elevation view of the fermentation vessel closure device of FIG. 22 taken generally in the direction of line 23—23 of FIG. 22.

Alternately, the elastic material forming cap 112' may not have any screw threads and be internally smooth, shown as cap 112" in FIG. 22 and FIG. 23. An upper part of cap 112" which receives the rim 110" projecting downwards is configured with a thickened cross section near the capping end so as to permit minimum deformation in case the cap is snugly fitted to a flask of slightly greater diameter. This ensures an air tight fit of the rim 110" to the mouth of the cap 112". The lower part of cap 112" which is adapted to assemble to the neck 120" of the fermentation vessel is made in relatively thin section to provide sufficient flexibility to receive any of a selected range of diameters of vessel neck 120".

In all embodiments, there is provided an improved fermentation vessel having a closure which, while permitting gas exchange, also permits easy access to the vessel contents and opening and closing by one hand manipulation.

While the invention has been described in terms of a series of specific embodiments, it is understood that these are intended as examples and not as limitations on the principles and scope of the invention. Further modifications and variations may be apparent to those skilled in the art, and the breadth of the invention is defined by reference to the claims which follow.

What is claimed is:

1. A closure for a fermentation vessel having an upper open end neck portion, comprising:

(a) a base member adapted to releasably attach to said neck portion in air-tight relation and having a planar wall portion shaped to cover the open end of the neck portion of said fermentation vessel, a retaining portion extending downwardly from said wall portion and shaped to releasably grasp said neck portion member in an air-tight relation, a nesting portion extending upwardly from said wall portion and shaped to permit nesting of components of a filtration-vent assembly therein and said wall portion having one or more first vent openings permitting passage of gas therethrough; and (b) a filtration-vent assembly shaped and adapted to rest and to be positionable on said base member wall portion and to nest within said nesting portion, said assembly comprising a pair of upper and lower planar wall members and between said wall members a planar gas pervious filter member, each said wall member having one or more second vent openings comparable in number, size and position to said wall portion first vent openings and aligned with an equal one or more vent openings in the other wall member, means operative to fix said wall and filter members relative to each other such that said wall and filter members can be moved together, said assembly being positionable on said wall portion such that said wall portion vent openings and said wall member vent openings may be sufficiently aligned to permit an aerobic operation within said vessel or misaligned to prevent such aerobic operation.

2. A closure for a fermentation vessel as claimed in claim 1 wherein said neck portion, wall portion, wall members and filter member are each substantially circular in shape.

3. A closure for a fermentation vessel as claimed in claim 2 wherein said retaining and nesting portions each comprise a circular rib extending respectively downwardly and upwardly from said wall portion.

4. A closure for a fermentation vessel as claimed in claim 2 wherein said one or more vent openings and said one or more wall member vent openings each comprise a pair of diametrically opposite circular openings.

5. A closure for a fermentation vessel as claimed in claim 1 including connecting means formed integral with and operative to hingedly connect said neck portion and base member.

6. A closure for a fermentation vessel as claimed in claim 2 including means formed integral with and extending upwardly from said upper wall member and providing when grasped means for rotating said filtration-vent assembly with respect to said wall portion.

7. A closure for a fermentation vessel as claimed in claim 3 wherein said upper wall member and filter member are each notched in similar positions and said lower wall member is formed with an upwardly extending rib having at least one inwardly extending projection located to engage said upper wall member and filter member notches such that said lower wall member, filter member and upper wall member may be rotatively fixed relative to one another.

8. A closure for a fermentation vessel as claimed in claim 2 wherein said wall portion includes an extension thereof extending beyond the boundaries of said neck portion and providing a means for grasping said wall portion to facilitate pivoting of said base member on said neck portion.

9. A closure for a fermentation vessel as claimed in claim 5 wherein said connecting means are formed in a manner to bias said base member away from said vessel neck portion when said wall portion first retaining portion is released from said neck portion.

10. A closure for a fermentation vessel as claimed in claim 3 wherein said base member nesting portion circular rib is formed with an inwardly turned lip operative to overlie and retain said assembly positioned on said base member wall portion.

11. A closure for a fermentation vessel as claimed in claim 1 wherein said base member is integrally formed with a tubular member operative to releasably engage the neck portion of said fermentation vessel in air-tight relation.

12. A closure for a fermentation vessel as claimed in claim 11 wherein said neck portion is formed with threads and said tubular member is formed with mating screw threads thereby enabling said tubular member and neck portion to be threadably secured together.

13. A closure for a fermentation vessel as claimed in claim 11 wherein said tubular member is formed of a sufficiently elastic material to adapt said tubular member to a neck portion of said fermentation vessel of any of a selected range of diameters.

* * * * *

UNITED STATES PATENT AND TRADEMARK OFFICE
CERTIFICATE OF CORRECTION

PATENT NO. : 5,395,006
DATED : March 7, 1995
INVENTOR(S) : Kuldeep Verma

It is certified that error appears in the above-indentified patent and that said Letters Patent is hereby corrected as shown below:

Column 2, line 12, correct "cad" to read --cap--.

Column 2, line 66, correct "are" to read --art--.

Signed and Sealed this

Twenty-fifth Day of April, 1995

*Attest:*

BRUCE LEHMAN

*Attesting Officer*     *Commissioner of Patents and Trademarks*